US009523159B2

(12) United States Patent
Hadba et al.

(10) Patent No.: US 9,523,159 B2
(45) Date of Patent: Dec. 20, 2016

(54) CROSSLINKED FIBERS AND METHOD OF MAKING SAME USING UV RADIATION

(75) Inventors: Ahmad Robert Hadba, Middlefield, CT (US); Sébastien Ladet, Lyons (FR)

(73) Assignees: Covidien LP, Mansfield, MA (US); SOFRADIM PRODUCTION, Trevoux (FR)

( * ) Notice: Subject to any disclaimer, the term of this patent is extended or adjusted under 35 U.S.C. 154(b) by 549 days.

(21) Appl. No.: 13/202,388

(22) PCT Filed: Feb. 22, 2010

(86) PCT No.: PCT/IB2010/000651
§ 371 (c)(1),
(2), (4) Date: Oct. 13, 2011

(87) PCT Pub. No.: WO2010/095055
PCT Pub. Date: Aug. 26, 2010

(65) Prior Publication Data
US 2012/0021015 A1     Jan. 26, 2012

Related U.S. Application Data

(60) Provisional application No. 61/154,382, filed on Feb. 21, 2009.

(51) Int. Cl.
C08J 3/22 (2006.01)
D01D 10/00 (2006.01)
D01F 6/78 (2006.01)

(52) U.S. Cl.
CPC .............. *D01D 10/00* (2013.01); *D01F 6/78* (2013.01)

(58) Field of Classification Search
CPC .......... A61L 31/00; A61L 31/02; A61L 31/04; A61L 31/14; D01F 6/04; D01F 6/28; D01F 6/30; D01F 6/44; D01F 6/46
USPC ..... 424/400; 525/407, 43, 56; 526/265, 287, 526/310, 347
See application file for complete search history.

(56) References Cited

U.S. PATENT DOCUMENTS

| | | |
|---|---|---|
| 3,767,085 A | 10/1973 | Cannon et al. |
| 4,326,532 A | 4/1982 | Hammar |
| 4,359,049 A | 11/1982 | Redl et al. |
| 4,464,321 A | 8/1984 | Pittalis et al. |
| 4,538,920 A | 9/1985 | Drake |
| 4,753,536 A | 6/1988 | Spehar et al. |
| 4,839,345 A | 6/1989 | Doi et al. |
| 4,857,403 A | 8/1989 | De Lucca et al. |
| 4,880,662 A | 11/1989 | Habrich et al. |
| 5,021,207 A | 6/1991 | De Lucca et al. |
| 5,372,585 A | 12/1994 | Tiefenbrun et al. |
| 5,455,308 A * | 10/1995 | Bastiaansen ............ 525/407 |
| 5,562,946 A | 10/1996 | Fofonoff et al. |
| 5,578,662 A | 11/1996 | Bennett et al. |
| 5,582,955 A | 12/1996 | Keana et al. |
| 5,612,050 A | 3/1997 | Rowe et al. |
| 5,804,318 A | 9/1998 | Pinchuk et al. |
| 5,889,140 A * | 3/1999 | Watanabe ............ 528/354 |
| 5,911,942 A | 6/1999 | Fofonoff et al. |
| 6,099,563 A | 8/2000 | Zhong |
| 6,103,317 A * | 8/2000 | Asai et al. ............ 427/512 |
| 6,107,365 A | 8/2000 | Bertozzi et al. |
| 6,107,453 A | 8/2000 | Zuccato et al. |
| 6,291,066 B1 * | 9/2001 | Branum ............ 428/364 |
| 6,312,725 B1 | 11/2001 | Wallace et al. |
| 6,342,591 B1 | 1/2002 | Zamora et al. |
| 6,451,032 B1 | 9/2002 | Ory et al. |
| 6,534,611 B1 | 3/2003 | Darling et al. |
| 6,552,103 B1 | 4/2003 | Bertozzi et al. |
| 6,570,040 B2 | 5/2003 | Saxon et al. |
| 6,576,000 B2 | 6/2003 | Carrison |
| 6,599,448 B1 * | 7/2003 | Ehrhard et al. ............ 252/582 |
| 6,624,245 B2 | 9/2003 | Wallace et al. |
| 6,881,766 B2 | 4/2005 | Hain |
| 6,958,212 B1 | 10/2005 | Hubbell et al. |
| 7,012,126 B2 | 3/2006 | Matsuda et al. |
| 7,105,629 B2 | 9/2006 | Matsuda et al. |
| 7,122,703 B2 | 10/2006 | Saxon et al. |
| 7,144,976 B2 | 12/2006 | Matsuda et al. |
| 7,172,877 B2 | 2/2007 | Ting |
| 7,247,692 B2 | 7/2007 | Laredo |
| 7,294,357 B2 | 11/2007 | Roby |
| 7,371,719 B2 | 5/2008 | Stupp et al. |
| 7,375,234 B2 | 5/2008 | Sharpless et al. |
| 7,560,588 B2 | 7/2009 | Breitenkamp et al. |
| 7,618,944 B2 | 11/2009 | Breitenkamp et al. |
| 7,638,558 B2 | 12/2009 | Breitenkamp et al. |

(Continued)

FOREIGN PATENT DOCUMENTS

| | | |
|---|---|---|
| BE | 1008260 A6 | 2/1996 |
| EP | 0490854 B1 | 9/1996 |

(Continued)

OTHER PUBLICATIONS

Q. Shi, et al., "The Immobilization of Proteins on Biodegradable Polymer Fibers via Click Chemistry", Biomaterials, 29, (2008), pp. 1118-1126.
Jérôme, et al., "Recent Advances in the Synthesis of Aliphatic Polyesters Ring-Opening Polymerization", Advanced Drug Delivery Reviews, 60, (2008), pp. 1056-1076.
Zhang, et al., "2-azido-2-deoxycellulose: Synthesis and 1,3-Dipolar Cycloaddition", Helvetica Chimica Acta, vol. 91, pp. 608-617 (2008).
R. Riva, et al., "Contribution of "Click Chemistry" to the Synthesis of Antimicrobial Aliphatic Copolyester", Polymer 49, (2008), pp. 2023-2028.
Baskin, et al., "Copper Free Click Chemistry for Dynamic In Vivo Imaging", PNAS, vol. 104, No. 43, (Oct. 23, 2007), pp. 16793-16797.

(Continued)

Primary Examiner — Micah-Paul Young

(57) ABSTRACT

Cross-linked fibers include first and second precursors, each possessing a core and at least one functional group known to have click reactivity when exposed to UV radiation. Mixtures of the first and second precursors are extruded to produce a filament and irradiated with UV light during the extrusion process.

12 Claims, 3 Drawing Sheets

(56) References Cited

U.S. PATENT DOCUMENTS

| | | | |
|---|---|---|---|
| 7,667,012 B2 | 2/2010 | Saxon et al. | |
| 7,795,355 B2 | 9/2010 | Matyjaszewski et al. | |
| 7,807,619 B2 | 10/2010 | Bertozzi et al. | |
| 7,981,444 B2 | 7/2011 | Tomalia et al. | |
| 7,985,424 B2 | 7/2011 | Tomalia et al. | |
| 8,034,396 B2 | 10/2011 | Kapiamba et al. | |
| 2002/0016003 A1 | 2/2002 | Saxon et al. | |
| 2002/0161170 A1 | 10/2002 | Matsuda et al. | |
| 2002/0169275 A1 | 11/2002 | Matsuda et al. | |
| 2002/0173616 A1 | 11/2002 | Matsuda et al. | |
| 2003/0100086 A1 | 5/2003 | Yao et al. | |
| 2003/0135238 A1 | 7/2003 | Milbocker | |
| 2003/0162903 A1 | 8/2003 | Day | |
| 2003/0199084 A1 | 10/2003 | Saxon et al. | |
| 2003/0205454 A1 | 11/2003 | Hlavinka et al. | |
| 2004/0170752 A1 | 9/2004 | Luthra et al. | |
| 2004/0185053 A1 | 9/2004 | Govindan | |
| 2004/0209317 A1 | 10/2004 | Ting | |
| 2004/0249438 A1 | 12/2004 | Lefranc et al. | |
| 2005/0032081 A1 | 2/2005 | Ju et al. | |
| 2005/0038472 A1 | 2/2005 | Furst | |
| 2005/0148032 A1 | 7/2005 | Saxon et al. | |
| 2005/0165164 A1* | 7/2005 | Moeller et al. | 525/66 |
| 2005/0222427 A1 | 10/2005 | Sharpless et al. | |
| 2005/0233389 A1 | 10/2005 | Ting et al. | |
| 2005/0244453 A1 | 11/2005 | Stucke et al. | |
| 2006/0018948 A1 | 1/2006 | Guire et al. | |
| 2006/0036022 A1 | 2/2006 | Callaghan et al. | |
| 2006/0085033 A1 | 4/2006 | Criscuolo et al. | |
| 2006/0108393 A1 | 5/2006 | Heinrich et al. | |
| 2006/0110782 A1 | 5/2006 | Bertozzi et al. | |
| 2006/0142404 A1 | 6/2006 | Berge et al. | |
| 2006/0147963 A1 | 7/2006 | Barone et al. | |
| 2006/0193865 A1 | 8/2006 | Govindan | |
| 2006/0228300 A1 | 10/2006 | Chang et al. | |
| 2006/0228357 A1 | 10/2006 | Chang et al. | |
| 2006/0240092 A1 | 10/2006 | Breitenkamp et al. | |
| 2006/0276658 A1 | 12/2006 | Saxon et al. | |
| 2007/0020620 A1 | 1/2007 | Finn et al. | |
| 2007/0037964 A1 | 2/2007 | Saxon et al. | |
| 2007/0060658 A1 | 3/2007 | Diaz et al. | |
| 2007/0077564 A1 | 4/2007 | Roitman et al. | |
| 2007/0086942 A1 | 4/2007 | Chang et al. | |
| 2007/0087001 A1 | 4/2007 | Taylor et al. | |
| 2007/0099251 A1 | 5/2007 | Zhang et al. | |
| 2007/0140966 A1 | 6/2007 | Chang et al. | |
| 2007/0178133 A1 | 8/2007 | Rolland | |
| 2007/0178448 A1 | 8/2007 | Tsao et al. | |
| 2007/0190597 A1 | 8/2007 | Agnew et al. | |
| 2007/0212267 A1 | 9/2007 | Organ et al. | |
| 2007/0244265 A1* | 10/2007 | Matyjaszewski et al. | 525/376 |
| 2007/0244296 A1 | 10/2007 | Tomalia et al. | |
| 2007/0249014 A1 | 10/2007 | Agnew et al. | |
| 2007/0254006 A1 | 11/2007 | Loose et al. | |
| 2007/0258889 A1 | 11/2007 | Douglas et al. | |
| 2007/0269369 A1 | 11/2007 | Gegg et al. | |
| 2007/0272122 A1 | 11/2007 | Lahann et al. | |
| 2007/0275387 A1 | 11/2007 | Ju | |
| 2007/0298006 A1 | 12/2007 | Tomalia et al. | |
| 2008/0015138 A1 | 1/2008 | Hamilton et al. | |
| 2008/0021486 A1 | 1/2008 | Oyola et al. | |
| 2008/0035243 A1 | 2/2008 | Breitenkamp et al. | |
| 2008/0038472 A1 | 2/2008 | Suzuki et al. | |
| 2008/0045686 A1 | 2/2008 | Meagher et al. | |
| 2008/0050731 A1 | 2/2008 | Agnew et al. | |
| 2008/0051541 A1* | 2/2008 | Strickler et al. | 526/265 |
| 2008/0051562 A1 | 2/2008 | Chaikof et al. | |
| 2008/0103564 A1 | 5/2008 | Burkinshaw et al. | |
| 2008/0121657 A1 | 5/2008 | Voegele et al. | |
| 2008/0125570 A1* | 5/2008 | Bojkova | 528/373 |
| 2008/0138317 A1 | 6/2008 | Fung | |
| 2008/0160017 A1 | 7/2008 | Baker et al. | |
| 2008/0166363 A1 | 7/2008 | Govindan et al. | |
| 2008/0171067 A1 | 7/2008 | Govindan et al. | |
| 2008/0187956 A1 | 8/2008 | Carrico et al. | |
| 2008/0199736 A1 | 8/2008 | Gadeken et al. | |
| 2008/0200628 A1 | 8/2008 | Gadeken et al. | |
| 2008/0207913 A1 | 8/2008 | Breitenkamp et al. | |
| 2008/0214436 A1 | 9/2008 | Yu et al. | |
| 2008/0214801 A1 | 9/2008 | Saxon et al. | |
| 2008/0214831 A1 | 9/2008 | Sharpless et al. | |
| 2008/0221043 A1 | 9/2008 | Harth et al. | |
| 2008/0241856 A1 | 10/2008 | Wong et al. | |
| 2008/0241892 A1 | 10/2008 | Roitman et al. | |
| 2008/0242171 A1 | 10/2008 | Huang et al. | |
| 2008/0248126 A1 | 10/2008 | Cheng et al. | |
| 2008/0267878 A1 | 10/2008 | Robillard et al. | |
| 2008/0283572 A1 | 11/2008 | Boyden et al. | |
| 2008/0311412 A1 | 12/2008 | Fokin et al. | |
| 2008/0317861 A1 | 12/2008 | Guan | |
| 2009/0012457 A1 | 1/2009 | Childers et al. | |
| 2009/0018646 A1 | 1/2009 | Zhao | |
| 2009/0027603 A1 | 1/2009 | Samulski et al. | |
| 2009/0038701 A1 | 2/2009 | Delmotte | |
| 2009/0053139 A1 | 2/2009 | Shi et al. | |
| 2009/0054619 A1 | 2/2009 | Baker et al. | |
| 2009/0061010 A1 | 3/2009 | Zale et al. | |
| 2009/0069561 A1 | 3/2009 | Fokin et al. | |
| 2009/0082224 A1 | 3/2009 | Haddleton et al. | |
| 2009/0099108 A1 | 4/2009 | Jones | |
| 2009/0124534 A1 | 5/2009 | Reineke et al. | |
| 2009/0137424 A1 | 5/2009 | Tsao et al. | |
| 2009/0181402 A1 | 7/2009 | Finn et al. | |
| 2009/0182151 A1 | 7/2009 | Wu et al. | |
| 2009/0202433 A1 | 8/2009 | Chang et al. | |
| 2009/0203131 A1 | 8/2009 | Reineke et al. | |
| 2009/0214755 A1 | 8/2009 | Armani et al. | |
| 2009/0220607 A1 | 9/2009 | Kiser et al. | |
| 2009/0240030 A1 | 9/2009 | Ju et al. | |
| 2009/0247651 A1 | 10/2009 | Kapiamba et al. | |
| 2009/0250588 A1 | 10/2009 | Robeson et al. | |
| 2009/0253609 A1 | 10/2009 | Fleury et al. | |
| 2009/0259016 A1 | 10/2009 | Johnson et al. | |
| 2009/0263468 A1 | 10/2009 | McAnulty et al. | |
| 2009/0269277 A1 | 10/2009 | Chang et al. | |
| 2009/0281250 A1 | 11/2009 | DeSimone et al. | |
| 2009/0297609 A1 | 12/2009 | Shoichet et al. | |
| 2009/0306310 A1 | 12/2009 | Wu et al. | |
| 2009/0312363 A1 | 12/2009 | Bradner et al. | |
| 2009/0325292 A1 | 12/2009 | Baker et al. | |
| 2010/0011472 A1 | 1/2010 | Hugel et al. | |
| 2010/0015046 A1 | 1/2010 | Govindan et al. | |
| 2010/0021391 A1 | 1/2010 | Douglas et al. | |
| 2010/0034862 A1 | 2/2010 | Laronde et al. | |
| 2010/0047258 A1 | 2/2010 | Wang et al. | |
| 2010/0048738 A1 | 2/2010 | Fleury et al. | |
| 2010/0069578 A1 | 3/2010 | Faust et al. | |
| 2010/0098640 A1 | 4/2010 | Cohen et al. | |
| 2010/0104589 A1 | 4/2010 | Govindan et al. | |
| 2010/0121022 A1 | 5/2010 | Musa et al. | |
| 2010/0159508 A1 | 6/2010 | Yang et al. | |
| 2010/0247433 A1 | 9/2010 | Tirrell et al. | |
| 2010/0286405 A1 | 11/2010 | Fokin et al. | |
| 2010/0291171 A1 | 11/2010 | Crescenzi et al. | |
| 2010/0303754 A1 | 12/2010 | Turpin et al. | |
| 2011/0008251 A1 | 1/2011 | Chang et al. | |
| 2011/0052696 A1 | 3/2011 | Hult et al. | |
| 2011/0060107 A1 | 3/2011 | Matyjaszewski et al. | |
| 2011/0143435 A1 | 6/2011 | Stayton et al. | |
| 2011/0177156 A1 | 7/2011 | Szoka, Jr. et al. | |
| 2011/0183417 A1 | 7/2011 | Reineke | |
| 2011/0213123 A1 | 9/2011 | Bertozzi et al. | |

FOREIGN PATENT DOCUMENTS

| | | |
|---|---|---|
| EP | 1790702 A1 | 5/2007 |
| EP | 1795563 A1 | 6/2007 |
| EP | 1975230 A1 | 1/2008 |
| EP | 2014308 A2 | 1/2009 |
| EP | 2090592 A1 | 8/2009 |
| GB | 737516 A | 9/1955 |
| WO | WO 2006/012569 A1 | 2/2006 |
| WO | WO 2007/041394 A2 | 4/2007 |
| WO | WO 2007/121055 A1 | 10/2007 |

(56) References Cited

FOREIGN PATENT DOCUMENTS

| WO | WO 2008/013618 A1 | 1/2008 | |
|---|---|---|---|
| WO | WO 2008/075955 A2 | 6/2008 | |
| WO | WO 2008/077406 A2 | 7/2008 | |
| WO | WO 2008/108736 A1 | 9/2008 | |
| WO | WO 2008/115694 A2 | 9/2008 | |
| WO | WO 2008/120016 A1 | 10/2008 | |
| WO | WO2008/138595 A1 | 11/2008 | |
| WO | WO 2008138595 A1 * | 11/2008 | ............... D01F 6/04 |
| WO | WO 2010/095049 A1 | 8/2010 | |

OTHER PUBLICATIONS

Codelli, et al., "Second Generation Difluorinated Cyclooctynes for Copper-Free Click Chemistry", J. Am. Chem. Soc., vol. 130, No. 34, (2008), pp. 11486-11493.

Sletten and Bertozzi, "A Hydrophilic Azacyclooctyne for Cu-free Click Chemistry", Org. Lett. (2008) 10(14), pp. 3097-3099.

Cazalis, et al., "C-Terminal Site-Specific PEGylation of a Truncated Thrombomodulin Mutant with Retention of Full Bioactivity", Bioconjugate Chem., (2004), 15, pp. 1005-1009.

Haridas, et al., "Design and Synthesis of Triazole-based Peptidedendrimers" Tetrahedron Letters, vol. 48, (2007), pp. 4719-4722.

Raghavan, et al., "Chemical Probes for Profiling Fatty Acid-associated Proteins in Living Cells", Bioorg. Med. Chem. Lett., 18 (2008), pp. 5982-5986.

LeDévédec, et al., "Separation of Chitosan Oligomers by Immobilized Metal Affinity Chromatography", Journal of Chromatography A., 2008, 1194(2), pp. 165-171.

Hartgerink, et al., "Peptide-amphiphile Nanofibers: A Versatile Scaffold for the Preparation of Self Assembling Materials", PNAS, 2002; 99(2), pp. 5133-5138.

Van Berkel, et al., "Metal-Free Triazole Formation as a Tool for Bioconjugation" Chem Bio Chem, 8, (2007), pp. 1504-1508.

Nottelet, et al., Synthesis of an X-ray opaque biodegradable copolyester by chemical modification of poly (ε-caprolactone) Biomaterials, 27, (2006), pp. 4943-4954.

Smith, et al., "Synthesis and Convenient Functionalization of Azide-labeled Diacyglycerol Analogues for Modular Access to Biologically Active Lipid Probes", Bioconjugate Chem, 19(9), (2008). pp. 1855-1863.

Skierka, et al., "The Influence of Different Acids and Pepsin on the Extractability of Collagen From the Skin of Baltic Cod (*Gadus morhua*)", Food Chemisty, 105, (2007), pp. 1302-1306.

Eastoe, "The Amino Acid Composition of Mammalian Collagen and Gelatin", vol. 61, (1955), pp. 589-600.

Sicherl, et al., "Orthogonally Protected Sugar Diamino Acids as Building Blocks for Linear and Branched Oligosaccharide Mimetics", Angew. Chem. Int. Ed. 44, (2005), pp. 2096-2099.

Laughlin, et al., "In Vivo Imaging of Membrane-Associated Glycans in Developing Zebrafish", Science, 320, (2008), pp. 664-667.

Worch and Wittmann, "Unexpected Formation of Complex Bridged Tetrazoles via Intramolecular 1,3-dipolar Cycloaddition of 1,2-0-cyanoalkylidene Derivatives of 3-azido-3-deoxy-D-allose", Carbohydrate Research, 343, (2008), pp. 2118-2129.

Witczak et al., "A Click Chemistry Approach to Glycomimetics: Michael addition of 2,3,4,6-tetra-O-acetyl-l-thio-β-D-glucopyranose to 4-deoxy-1,2-O-isopropylident-L-*glycero*-pent-4-enopyranos-3-ulose-a convenient route to novel 4-deoxy-(1→5)-5-C-thiodisaccharides", Carbohydrate Research, 342, (2007), 1929-1933.

Marra, et al., "Validation of the Copper(1)-Catalyzed Azide-Alkyne Coupling in Ionic Liquids, Synthesis of a Triazole-Linked C-Disaccharide as a Case Study", J. Org. Chem (2008), 73(6), pp. 2458-2461.

Srinivasachari, et al., "Versatile Supramolecular pDNA Vehicles via "Click Polymerization" of β-cyclodextrin with oligoethyleneamines", Biomaterials, 30, (2009), pp. 928-938.

Arora, et al., "A Novel domino-click approach for the synthesis of sugar based unsymmetrical bis- 1,2,3-triazoles", Carbohydrate Research, 343, (2008), 139-144.

Chen, et al., "Synthesis of a $C_3$-symmetric (1→6)-N-acetyl-β-D-glucosamine Octadecasaccharide using Click Chemistry", Carbohydrate Research, 340, (2005), pp. 2476-2482.

Gouin, et al., "Multi-Mannosides Based on a Carbohydrate Scaffold: Synthesis, Force Field Development, Molecular Dynamics Studies, and Binding Affinities for Lectin Con A", J. Org. Chem., 2007, 72(24), pp. 9032-9045.

Srinivasachari, et al., "Effects of Trehalose Click Polymer Length on pDNA Complex Stability and Delivery Efficacy", Biomaterials, 28, (2007), pp. 2885-2898.

Godeau, et al., Lipid-Conjugated Oligonucleotides via "Click Chemistry" Efficiently Inhibit Hepatitis C Virus Translation, J. med. Chem., 2008, 51(15), pp. 2374-4376.

Zou et al., "Cu-free Cycloaddition for Identifying Catalytic Active Adenylation Domains of Nonribosomal Peptide Synthesis by phage display", Bioorganic & Medicinal Chemistry Letters, 18 (2008), pp. 5664-5667.

Cantel, et al., "Synthesis and Conformational Analysis of a Cyclic Peptide Obtained via *i* to *i* + 4 Intramolecular Side-chain to Side-chain Azide-Alkyne 1,3-Dipolar Cycloaddition" J. Org. Chem., 2008, 73 (15), pp. 5663-5614.

Dijk, et al., Synthesis of Peptide-Based Polymers by Microwave-Assisted Cycloaddition Backbone Polymerization, Biomacro molecules, 2007, 8(2), pp. 327-330.

Köster, et al., "Spectroscopic and Electrochemical Studies of Ferroceryl Triazole Amino Acid and Peptide Bioconjugates Synthesized by Click Chemistry", Organometallics, 2008, 27(23) pp. 6326-6332.

Dijk, et al., "Synthesis and Characterization of Biodegradable Peptide-Baed Polymers Prepared by Microwave-Assisted Click Chemisty", Biomacromolecules, 2008, 9(10), pp. 2834-2843.

Jiang, et al., "Amphiphilic PEG/alkyl-grafted comb polylactides", J. Polymer Science Part B: Polymer Physics, 45(22), 2007, pp. 5227-5236.

Ochs, et al., "Low-Fouling, Biofunctionalized, and Biodegradable Click Capsules", Biomacromolecules, 2008, 9(12), pp. 3389-3396.

Beatty and Tirrell, "Two-color Labeling of Temporally Defined Protein Populations in Mammalian Cells", Bioorg. Med. Chem. Lett., 18 (2008), pp. 5995-5999.

Kolb, et al., "Click Chemistry: Diverse Chemical Function from a Few Good Reactions", Angewandte Chemie, International Edition, Jun. 2001, pp. 2004-2021.

Krouit, et al., "Cellulose surface grafting with polycaprolactone by heterogeneous click-chemistry", European Polymer Journal 44, Dec. 2008, pp. 4074-4081.

Nandivada, et al. "Reactive polymer coatings that 'Click'.", Angewandte Chemie, International Edition 45, Apr. 2006, pp. 3360-3363.

Ossipov and Hilborn, Poly(vinyl alcohol)-Based Hydrogels Formed by "Click Chemistry", Macromelecules 2006, 39, pp. 1709-1718.

Binder and Sachsenhofer, "Click Chemistry in Polymer and Materials Science", Macromolecular Rapid Commun. 2007, 28, pp. 15-54.

International Search Report for PCT/IB10/000651 date of completion is May 18, 2010 (2 pages).

* cited by examiner

CROSSLINKED FIBERS AND METHOD OF MAKING SAME USING UV RADIATION

CROSS-REFERENCE TO RELATED APPLICATIONS

This application is a U.S. National Stage Application filed under 35 U.S.C. §371(a) of International Application No. PCT/IB2010/000651 filed Feb. 22, 2010, which claims the benefit of and priority to U.S. Provisional Application Ser. No. 61/154,382 filed Feb. 21, 2009, the entire contents of which are incorporated by reference herein.

BACKGROUND

Technical Field

The present disclosure relates to crosslinked fibers, and more particularly to the use of click chemistry to form the crosslinked fibers using UV radiation, methods of preparing such fibers, and surgical devices made from such fibers.

Background of Related Art

Methods for making monofilaments that are suitable to fabricate surgical articles, such as sutures, generally include the steps of extruding at least one bioabsorbable or nonbioabsorbable polymer to provide filaments, drawing or stretching the solidified filaments to achieve molecular orientation, and annealing the drawn filaments to relieve internal stresses.

Various spinning methods may be employed, such as melt spinning, wet or dry solvent spinning, and reaction spinning. Melt spinning uses heat to melt the fiber polymer to a viscosity suitable for extrusion through the spinneret. Solvent spinning uses large amount of organic solvents to dissolve the fiber polymer into a fluid polymer solution suitable for extrusion through a spinneret. Reaction spinning involves the formation of filaments from prepolymers and monomers that are further polymerized and cross-linked after the filament is formed.

Click chemistry refers to a collection of supremely reliable and self-direct organic reactions which is capable of forming a highly reliable molecular connection in solution or bulk state. Click chemistry reactions may be highly selective, high yield reactions which should not interfere with one another as well as other reactions.

It would be desirable to make filaments useful in making surgical devices by extruding a mixture containing first and second precursors functionalized for crosslinking by click chemistry using UV as a reaction catalyst.

SUMMARY

A first aspect of the present invention is a process comprising:
mixing first and second precursors, each of the first and second precursors possessing a core and at least one functional group known to have click reactivity when exposed to UV radiation; and
extruding the first and second precursors through an extrusion unit to produce a filament,
exposing the first and second precursors to UV radiation.

In the present application, unless otherwise specified, the expressions "functional group", "functional unit", "functionality", "functional group known to have click reactivity", "reactive group" and "reactive member" in relation to the first and second precursors are used interchangeably to designate a functional group known to have click reactivity, in particular when exposed to UV radiation. In the present application, the expression "functionalized" in relation to the first and second precursors designates the first and second precursor with a functional group attached thereto.

Another aspect of the invention is a filament obtained by:
mixing first and second precursors, each of the first and second precursors possessing a core and at least one functional group known to have click reactivity when exposed to UV radiation; and
extruding the first and second precursors through an extrusion unit to produce a filament,
exposing the first and second precursors to UV radiation.

In embodiments, at least one of the first or second precursors is functionalized with one or more thiol groups.

In embodiments, at least one of the first or second precursors is functionalized with one or more alkene groups.

In embodiments, the at least one functional group of the first precursor is a thiol group and the at least one functional group of the second precursor is an alkene group.

In embodiments, the first precursor and optionally the second precursor comprises a polyol core. For example, the polyol is selected from the group consisting of polyethers, polyesters, polyether-esters, polyalkanols, and combinations thereof.

Another aspect of the invention is a filament comprising UV cross-linked first and second precursors each functionalized with a plurality of functional group known to have click reactivity when exposed to UV radiation.

Another aspect of the invention is a medical device comprising a filament as described above or obtained by a process as described above.

Cross-linked fibers in accordance with the present disclosure are made from a mixture of first and second precursors each having at least at least one functional group known to have click reactivity when exposed to UV radiation. The first and second precursors may each possess a core functionalized with a reactive member. Suitable components for use as the core(s) include, but are not limited to, monomers, oligomers, macromers, polymers, and the like. In embodiments, the first precursor possesses at least one thiol group and the second precursor possesses at least one alkene group.

The present disclosure also relates to a method of forming cross-linked fibers. First and second precursors, each possessing a core and at least one functional group known to have click reactivity upon exposure to UV radiation, are mixed. The mixed precursors are then extruded through an extrusion unit to produce a filament. Cross-linking of the first and second precursors is then achieved by exposing the fiber to UV light.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure.

DETAILED DESCRIPTION OF THE EMBODIMENTS

Figure 1:
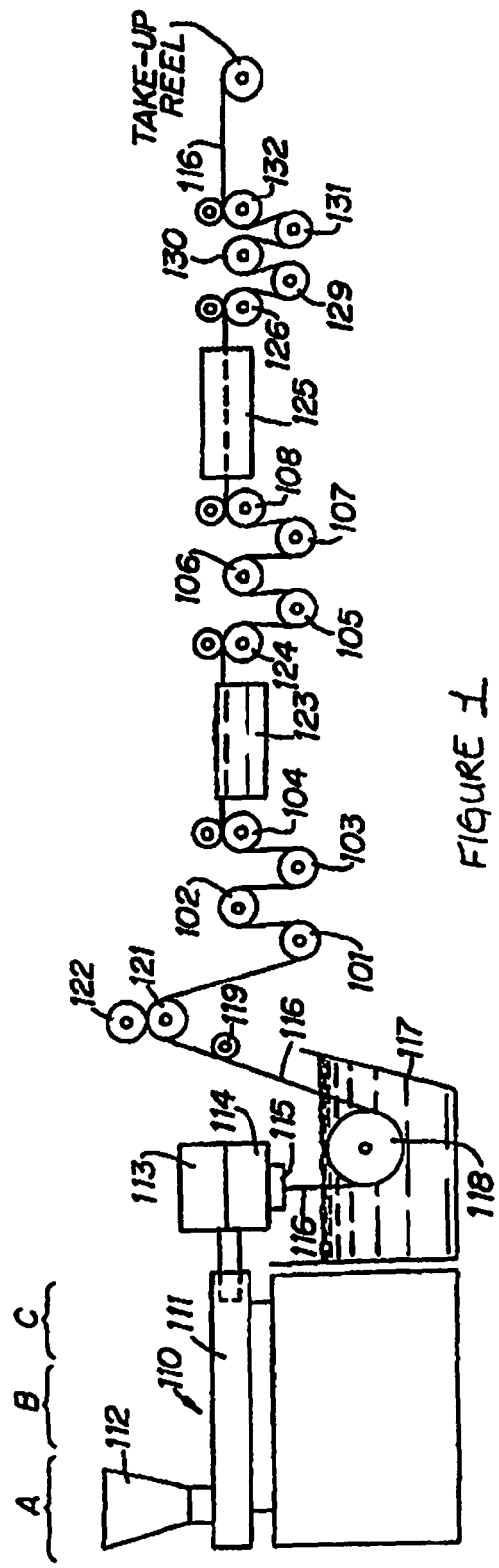
FIG. 1 is a schematic illustration of an apparatus which is suitable for carrying out a fiber manufacturing process in accordance with the present disclosure.

Cross-linked fibers in accordance with the present disclosure are made from a mixture of first and second precursors each having at least at least one functional group known to have click reactivity when exposed to UV radiation.

The Core Component

The core of the first and second precursors may be any suitable biocompatible material. Thus, the fibers may be prepared from any first and second precursors known to form biocompatible polymers. In embodiments, the first and second precursors may be different materials, thus forming copolymer filaments. The fibers may be formed from a natural material or a synthetic material. The material from which the fibers are formed may be bioabsorbable or non-bioabsorbable. It should of course be understood that any combination of natural, synthetic, bioabsorbable and non-bioabsorbable materials may be used to form the fibers. Such cores may thus be linear, branched, star-shaped, dendrimeric, and the like.

In embodiments, suitable cores for use as the first precursor, the second precursor, or both, may be prepared from a polyol, a polyamine, or a polythiol. In embodiments a polyol may be used to form a core. Examples of such polyols include, in embodiments, polyethers, polyesters, polyether-esters, polyalkanols, combinations thereof, and the like.

Suitable polyethers which may be utilized in forming the core of the first precursor and/or the second precursor are within the purview of those skilled in the art and include, for example, poly(ethylene glycol), polypropylene glycol, polybutylene glycol, polytetramethylene glycol, polyhexamethylene glycol, copolymers thereof such as cyclodextrin-poly(ethylene glycol)s, polyacetals, and combinations thereof. In embodiments a suitable polyether may include poly(ethylene glycol).

Suitable polyesters which may be utilized in forming the core of the first precursor and/or the second precursor are within the purview of those skilled in the art and include, for example, trimethylene carbonate, ε-caprolactone, p-dioxanone, glycolide, lactide, 1,5-dioxepan-2-one, polybutylene adipate, polyethylene adipate, polyethylene terephthalate, and combinations thereof.

In addition, as noted above, the first precursor and/or the second precursor may include a poly(ether-ester) block. Any suitable poly(ether-ester) block within the purview of those skilled in the art may be utilized. These macromers may include an aliphatic diacid, aromatic diacid, alicyclic diacid, or combinations thereof, linking two dihydroxy compounds (sometimes referred to herein as a "poly(ether-ester) macromer"). Up to ten repeats of the poly(ether-ester) macromer may be present.

Suitable diacids which may be utilized in forming the poly(ether-ester) macromer include, for example, diacids having from about 2 to about 10 carbon atoms. Suitable diacids include, but are not limited to, sebacic acid, azelaic acid, suberic acid, pimelic acid, adipic acid, glutaric acid, succinic acid, malonic acid, oxalic acid, terephthalic acid, cyclohexane dicarboxylic acid, and combinations thereof.

Suitable dihydroxy compounds which may be utilized in forming the poly(ether-ester) macromer include, for example, polyols including polyalkylene oxides, polyvinyl alcohols, polycaprolactone diols, and the like. In some embodiments, the dihydroxy compounds can be a polyalkylene oxide such as polyethylene oxide ("PEO"), polypropylene oxide ("PPO"), block or random copolymers of polyethylene oxide (PEO) and polypropylene oxide (PPO), and combinations thereof.

In one embodiment, a poly(ethylene glycol) ("PEG") may be utilized as the dihydroxy compound. It may be desirable to utilize a PEG with a molecular weight of from about 200 g/mol to about 10000 g/mol, in embodiments from about 400 g/mol to about 900 g/mol. Suitable PEGs include those commercially available from a variety of sources under the designations PEG 200, PEG 400, PEG 600 and PEG 900.

Any method may be used to form the poly(ether-ester) macromer. In some embodiments, the poly(ether-ester) macromer may be formed by combining adipoyl chloride with a PEG such as PEG 600 and pyridine in a suitable solvent, such as tetrahydrofuran (THF). The solution may be held at a suitable temperature, from about −70° C. to about 25° C., for a period of time of from about 4 hours to about 18 hours, after which the reaction mixture may be filtered to remove the precipitated pyridine hydrochloride by-product and the resulting poly(ether-ester) macromer, here a PEG/adipate compound. The resulting poly(ether-ester) macromer may be obtained from the solution by the addition of an ether or petroleum ether, and collected by suitable means which can include filtration. Other methods suitable for producing such macromers are within the purview of those skilled in the art.

In embodiments, components utilized in forming poly(ether-esters) may be functionalized and reacted to form poly(ether-ester-urethanes), poly(ether-ester-ureas), and the like.

Other examples of suitable poly(ether-ester) blocks which may be utilized include, but are not limited to, poly(ethylene glycol)-polycaprolactone, poly(ethylene glycol)-polylactide, poly(ethylene glycol)-polyglycolide, and various combinations of the individual polyethers and polyesters described herein. Additional examples of suitable poly(ether-ester) blocks include those disclosed in U.S. Pat. No. 5,578,662 and U.S. Patent Application No. 2003/0135238, the entire disclosures of each of which are incorporated by reference herein.

In embodiments, the resulting poly(ether-ester) macromer may be of the following formula:

$$HO—(X-A)_y-X—OH \qquad (I)$$

wherein A is a group derived from an aliphatic, aromatic, or alicyclic diacid; X can be the same or different at each occurrence and may include a group derived from a dihydroxy compound; and y may be from about 1 to about 10. In some embodiments, the A group can be derived from adipic acid, and X can be derived from a poly(ethylene glycol) having a molecular weight of from about 200 g/mol to about 1000 g/mol, in embodiments from about 400 g/mol to about 800 g/mol, in embodiments about 600 g/mol.

The molecular weight and viscosity of these compounds may depend on a number of factors such as the particular diacid used, the particular dihydroxy compound used, and the number of repeat units present. Generally, the viscosity of these compounds may be from about 300 to about 10,000 cP at 25° C. and a shear rate of 20.25 sec$^{-1}$.

In other embodiments, polyrotaxanes may be utilized as the core of the first precursor, the second precursor, or both. Polyrotaxane materials include cyclic molecules, linear molecules threaded through the cyclic molecules, and optionally bulky end groups on the linear molecules to prevent the loss of the cyclic molecules by dethreading. With respect to rotaxanes, "linear molecules" refers to any suitable molecules, whether branched or unbranched, that are capable of threading the cyclic molecules to form the rotaxane material. The linear molecules are generally in the form of chains that are unbranched. Branching of the linear molecules may occur, but not to the extent that the branching significantly interferes with the formation of the rotaxane material.

Examples of suitable polyrotaxanes include those created by linear polymers such as poly(ethylene oxide) (PEO) penetrating the inner cavity of cyclodextrins (CDs) to form inclusion complexes with a necklace-like supramolecular structure.

In addition to the polyols described above, in embodiments a polyamine and/or a polythiol may be used to form a core of first and/or second precursors herein.

In embodiments, the polyol, such as a polyether, polyester, or polyether-ester as described above, may be a branched polyol. Such a polyol may have a central core from which from about 3 to about 12 arms may extend, with hydroxyl groups at the free terminal of each arm. In embodiments, the polyol, such as a polyether, polyester, or polyether-ester as described above, may be endcapped with functional groups.

The Reactive Groups

The first precursor and the second precursor each have at least one reactive member known to have click reactivity when exposed to UV radiation. In embodiments, the precursors may have from about 2 to about 50 reactive members. The click chemistry reaction of the present disclosure includes first and second precursors each having terminal and/or side chain functionality. The first and second precursors are functionalized by converting an attached functional unit on the precursor thereby providing site specific functional materials, site specific functional materials comprising additional functionality, or chain extended functional materials. Optionally, a linker may or may not be present for linking a functional group to the precursor. These reactive members may form arms extending from the core(s). Such cores may thus be linear, branched, star-shaped, dendrimeric, and the like.

Click chemistry refers to a collection of reactive members having a high chemical potential energy capable of producing highly selective, high yield reactions. The reactive members react to form extremely reliable molecular connections in most solvents, including physiologic fluids, and often do not interfere with other reagents and reactions. Examples of click chemistry reactions include Huisgen cycloaddition, Diels-Alder reactions, thiol-alkene reactions, and maleimide-thiol reactions.

The thiol moieties may be selected from any suitable compound having a sulfur atom and a hydrogen atom (—SH). Alkene or olefin moieties may be selected from any suitable compound having a carbon double bond (C=C).

The thiol-alkene (thiol-ene) reaction is a hydrothiolation, i.e., addition of RS—H across a C=C bond. The thiol-ene reaction proceeds via a free-radical chain mechanism. Initiation occurs by radical formation upon UV excitation of a photoinitiator or the thiol itself. Thiol-ene systems form ground state charge transfer complexes and therefore photopolymerize even in the absence of initiators in reasonable polymerization times. However, the addition of UV light increases the speed at which the reaction proceeds. The wavelength of the light can be modulated as needed, depending upon the size and nature of the constituents attached to the thiol or alkene. A general thiol-ene coupling reaction mechanism is represented below:

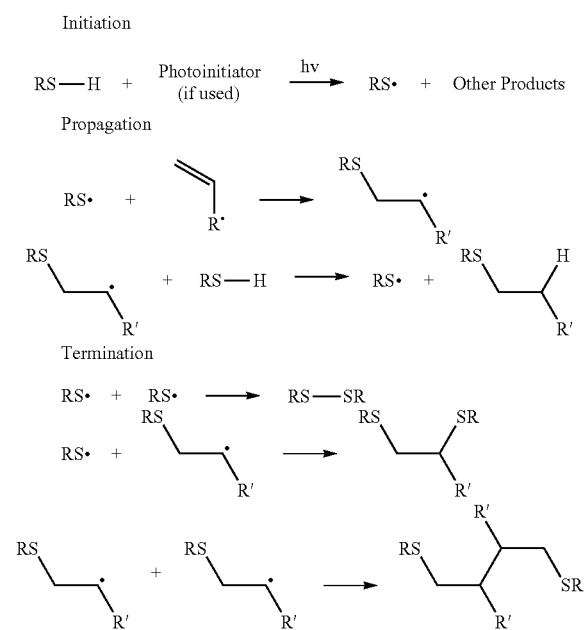

Those skilled in the art reading this disclosure will readily envision chemical reactions for activating other core materials to render them suitable for use as precursors in the presently described methods.

Forming the Fiber

To form a fiber, the first and second precursors may take the form of any solution, suspension, semi-solid, or solid material capable of allowing the two precursors to interact and crosslink. The first and second precursors may be in granular, pellet, or powder form, or alternatively, may be in a dilute solution. Suitable solvents which may be utilized to form a dilute solution include any biocompatible solvent within the purview of those skilled in the art which will not interfere with the reaction of the reactive groups of the first and second precursors. Suitable solvents which may be utilized include, for example, polar solvents such as water, ethanol, triethylene glycol, dimethyl sulfoxide, glymes (such as diglyme, triglyme, tetraglyme, and the like), poly(ethylene glycol)s, methoxy-poly(ethylene glycol)s, dimethylformamide, dimethylacetamide, gamma-butyrolactone, n-methylpyrollidone, ketones such as methyl ethyl ketone, cyclohexanone, diethylene glycol momethyl ether acetate, diethylene glycol monobutyl ether acetate, diethylene glycol monomethyl ether, diethylene glycol monoethyl ether, diethylene glycol monobutyl ether, diethylene glycol monoisobutyl either, diisobutyl ketone, diacetone alcohol, ethyl amyl ketone, ethyl lactate, and the like. In other embodiments, solvents such as tetrahydrofuran, ethyl acetate, isopropyl acetate, butyl acetate, isopropanol, butanol, acetone, and the like, may be utilized. In embodiments, combinations of any of the foregoing solvents may be utilized to form a dilute solution. The amount of solvent used will depend on a number of factors, including the particular first precursor, second precursor, or combination thereof that are to be employed and the intended end use of the composition.

The first and second precursors may be placed in a hopper and mixed thoroughly to provide substantially uniform distribution of the first precursor among the second precursor. The first and second precursors may be mixed using any conventional technique, with or without heating. For example, a mechanical mixer, a static mixer, or combinations thereof, may be employed to assist in providing a substantially uniform distribution of first and second precursors. After mixing, the mixture is extruded or spun to form one or more filaments. A UV catalyst is introduced during the extrusion process to aid in polymerization of the first and second precursors into filaments.

Initiation of polymerization is accomplished by irradiation with light at a wavelength of between about 20-400 nm, in the ultraviolet range. The UV radiation may be obtained from sunlight or special lamps or light sources which emit UV light having a wavelength in the range above. Particularly, thiol-ene polymerizations are photochemically initiated, step growth, free-radical processes that take place between thiols and alkenes via a sequential propagation/chain-transfer process. Thiol-ene systems form ground state charge transfer complexes, and therefore photopolymerize even in the absence of initiators in reasonable polymerization times. Since the complex which absorbs the light is consumed by the polymerization, the polymer itself does not absorb light. Where the fiber is opaque, UV irradiation will provide only surface cross-linking. Where the fiber is transparent or translucent (e.g., while still molten or in solution), exposure to UV radiation may result in bulk cross-linking.

The first and second precursors may be irradiated with light at one or more points in the extrusion process. For example, after exiting the spinneret the fiber may be irradiated while the still in the molten state. As another example, prior to wind up, the formed and annealed fiber may be irradiated with UV light to crosslink the finished fiber.

The rate of cross-linking of the first and second precursors of the present disclosure may be tailored by controlling the concentration of the first precursor and the second precursor. Generally, a faster cross-linking time may be observed at a higher concentration of either the first or second precursors than the rate observed for the same components at a lower concentration. In embodiments, the ratio of first precursor reactive groups to second precursor reactive groups is from about 1:2 to about 1:1. Alternatively, cross-linking time can be controlled by varying the UV intensity or exposure time.

FIG. 1 schematically illustrates an illustrative filament manufacturing operation in accordance with the disclosure. Extruder unit 110 is equipped with controls for regulating the temperature of barrel 111 in various zones thereof, e.g., progressively higher temperatures in three consecutive zones, A, B, and C along the length of the barrel. The first and second precursors to be spun into filaments are introduced to the extruder through hopper 112. Prior to or during placement in hopper 112, the first precursor is combined with the second precursor and mixed in a one-pot process. In embodiments, a UV light may be present along a portion of the barrel to aid in the polymerization of the first and second precursors.

Motor-driven metering pump 113 delivers the melt extruded first and second precursor mixture at a constant rate and with high pressure to spin pack 114 and thereafter through an extrusion die or spinneret 115 possessing one or more orifices of desired diameter to provide a molten monofilament 116.

The molten monofilament 116 then enters quench bath 117, e.g., containing water, where the monofilament solidifies. The distance monofilament 116 travels after emerging from spinneret 115 to the point where it enters quench bath 117, i.e., the air gap, can vary. If desired, a chimney (not shown), or shield, can be provided to isolate monofilament 116 from contact with air currents which might otherwise affect the cooling of the monofilament in an unpredictable manner. In general, barrel zone A of the extruder can be maintained at a temperature of from about 100° C. to 220° C., zone B at from about 160° C. to 230° C. and zone C at from about 170° C. to about 240° C. Additional temperature parameters include: metering pump block 113 at from about 170° C. to about 230° C., spin pack 114 at from about 170° C. to about 230° C., spinneret 115 at from about 170° C. to about 230° C. and quench bath at from about 10° C. to about 80° C.

Monofilament 116 is passed through quench bath 117 around driven roller 118 and over idle roller 119. Optionally, a wiper (not shown) may remove excess water from the monofilament as it is removed from quench bath 117. In embodiments, the quench bath 117 may be irradiated with UV light. A lamp my illuminate the solution of the bath to aid in the polymerization of the formed filaments.

On exiting the quench bath the monofilament is wrapped around a first godet 121 provided with nip roll 122 to prevent slippage which might otherwise result from the subsequent stretching operation; and subsequently wrapped around godets 101, 102, 103 and 104 or any other suitable godet arrangement. Monofilament 116 passing from godet 104 is stretched, e.g., with stretch ratios on the order of from about 3:1 to about 10:1 and preferably from about 4:1 to about 7:1, to effect its orientation and thereby increase its tensile strength.

In the stretching operation, monofilament 116 may be drawn through hot water (or other suitable liquid medium) draw bath 123 by means of godets 124, 105, 106, 107 and 108 or any other suitable arrangement of godets which rotate at a higher speed than godet 104 to provide the desired stretch ratio. The temperature of hot water draw bath 123 is advantageously from about 30° C. to about 90° C. and preferably is from about 30° C. to about 50° C. In an alternative stretching operation, generally preferred for smaller sutures sizes, e.g., sizes 3/0 to 8/0, monofilament 116 may be drawn by godets 124, 105, 106, 107, and 108 or any other suitable godet arrangement through hot air convection oven chamber 123 at a temperature of from about 30° C. to about 140° C., and preferably from about 50° C. to about 130° C. to provide the desired amount of stretch.

Following the stretching operation, monofilament 116 optionally may be subjected to an on-line annealing and/or additional stretching without shrinkage or relaxation with shrinkage operation as a result of which the monofilament shrinks. In the process of FIG. 1, on-line annealing with or without relaxation when desired is accomplished by driving monofilament 116 by godets 126, 129, 130, 131, and 132 or any other suitable godet arrangement through second hot air oven chamber 125 at a temperature of from about 40° C. to about 150° C., and preferably from about 60° C. to about 130° C. During the relaxation process, at these temperatures, monofilament 116 will generally recover to within about 80 to about 97 percent, and preferably to within about 95 percent, of its pre-annealed length to provide the finished suture. For relaxation, the third godet rotates at a slower speed than the second godet thus relieving tension on the filament.

Annealing of the filaments also may be accomplished without shrinkage of the suture. In carrying out the annealing operation, the desired length of suture may be wound around a creel and the creel placed in a heating cabinet maintained at the desired temperature, e.g. about 60° C. to about 130° C. After a suitable period of residency in the heating cabinet, e.g., about 18 hours or so, the suture will have undergone essentially no shrinkage. The creel may be rotated within the heating cabinet in order to insure uniform heating of the monofilament or the cabinet may be of the circulating hot air type in which case uniform heating of the monofilament will be achieved without the need to rotate the creel. Thereafter, the creel with its annealed suture is removed from the heating cabinet and when returned to room temperature, the filament is removed from the creel, conveniently by cutting the wound monofilament at opposite ends of the creel. The annealed filaments are then ready to be packaged and sterilized or formed into other surgical devices.

In embodiments, cross-linked fibers from chitin or chitin derivative cores that have been functionalized with first and second precursors each having at least at least one functional group known to have click reactivity in the presence of UV light can be produced according to the present disclosure by spinning from anisotropic solution. Suitable methods for solution spinning chitin or chitin derivative fibers are generally disclosed in European Patent Nos. EP0328050A2 and EP0077098A2, the entire disclosures of which are incorporated herein by this reference. Such fibers can have tensile properties which typically fall between 4-8 g/d tenacity and 150-250 g/d initial modulus.

High strength cross-linked chitosan fibers can be prepared by spinning an aniostropic solution of appropriately functionalized chitosan or a derivative of chitin or chitosan through an inert gas and into a coagulating bath, removing the as-spun fiber and treating it with alkali to remove N-acetyl, O-acetyl or other pendant groups at the 2, 3 and 6 carbon positions of the glucosamine repeating unit. Treatment of fibers is by immersion of the fibers into a solution of NaOH. With fine denier fibers, e.g., 4-5 dpf., a 5 minute immersion at 70° C. in a 50% wt. solution of NaOH is satisfactory. A 2-3 hr. exposure at 80° C. in a 30% wt. solution is useful with chitosan acetate formate fiber. With chitosan acetate, temperatures in the range of 80° to 116° C. at NaOH concentration of 30% have been found useful with the higher temperatures requiring less time for completion of the reaction. Severe treatments are generally to be avoided since they may cause excessive interfilament fusion and a product of inferior quality. Conversion of the starting fiber to a chitosan fiber is confirmed if the chitosan fiber is readily soluble in dilute (3-20% wt.) acetic acid.

Figure 2:
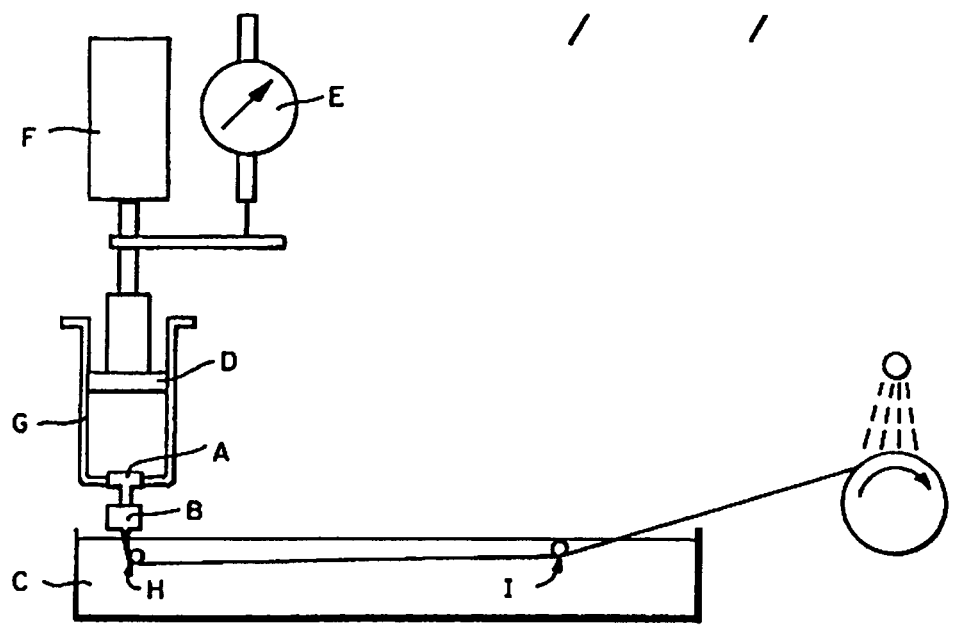
FIG. 2 is a schematic illustration of another apparatus which is suitable for carrying out a fiber manufacturing process in accordance with the present disclosure.

In using the apparatus of FIG. 2 an anisotropic solution of chitin or a chitin derivative is placed in spin cell (G). A piston (D) activated by hydraulic press (F) and associated with piston travel indicator (E) is positioned over the surface of the solution, excess air is expelled from the top of the cell and the cell is sealed. The spin cell is fitted at the bottom with the following screens (A) for solution filtration: four to six 325-mesh screens. The filtered solution is then passed into a spinneret pack (B) containing two or three 325-mesh screens. Solutions are extruded through an air gap at a controlled rate into a static bath (C) using a metering pump to supply pressure at piston (D). The fiber is passed around a pin (H), pulled through the bath, passed under a second pin (I) and wound onto a bobbin. The air gap between the spinneret face and the coagulation bath is typically 0.6 to 2.0 cm. The coagulation bath temperature is generally held below 100° C.

Figure 3:
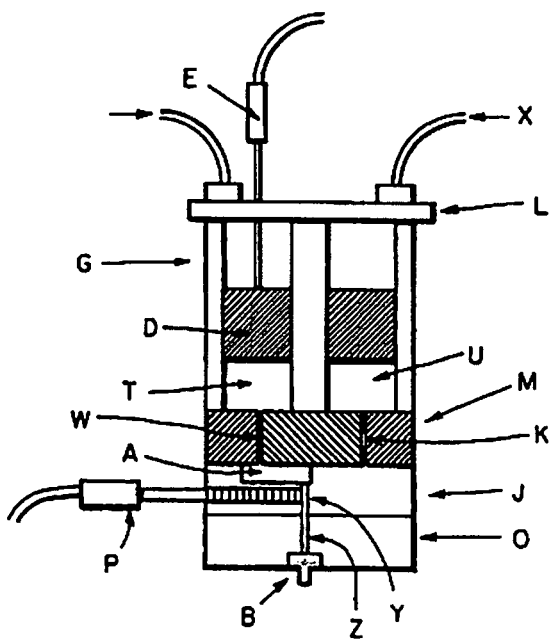
FIG. 3 is a cross-sectional view of yet another embodiment of a fiber manufacturing process.

In using the apparatus of FIG. 3, filter plate (J) is replaced by mixing plate (R). Polymer dope is placed in cylinder bore (T) and then piston (D) and cap plate (L) is fitted to the spin cell (G). A driver fluid (e.g. water) is pumped into the upper part of bore (T) through feed line (F). The piston (D) is displaced by the driver fluid, thereby pushing the polymer dope through passages (W), (S) in mixing plate (R) and then through passage (K) in distribution plate (M) into second cylinder bore (U). This process is then reversed by pumping fluid through feed line (X). The aforementioned forward and reverse process is repeated several times to effect a mixing of the polymer dope. Component (E) acts to sense the position of cylinder (D).

After mixing is complete (about 30 cycles), mixing plate (R) is replaced by filter plate (J) and polymer dope is extruded from bore (T) through passage (W), through filter pack (A) containing 2 Dutch Twill Weave 165×800 mesh screens, through passage (Y) in filter plate (J) and passage (Z) in spinneret mounting plate (O) and out of spin cell (G) through spinneret (B). The extruded dope is spun into a bath and taken up as described for FIG. 4. Pressure of the polymer dope during spinning is measured by pressure transducer (P).

As noted previously, the first and second precursors may be irradiated with a UV light at one or more points in the extrusion process. For example, a source of UV radiation may be provided immediately after the spinneret (B). As yet another example, a source of UV radiation may be provided as the filament exits static bath (C). As yet another example, a source of UV radiation may be provided as the filament is passed under second pin (I) and wound onto the bobbin.

In other embodiments, cross-linked fibers from collagen or collagen derivative cores that have been functionalized with click reactive groups can be produced according to the present disclosure by gel spinning. Suitable methods for gel spinning collagen fibers in general are disclosed in U.S. Pat. Nos. 5,562,946 and 5,911,942, the entire disclosures of which are incorporated herein by this reference.

Figure 4:
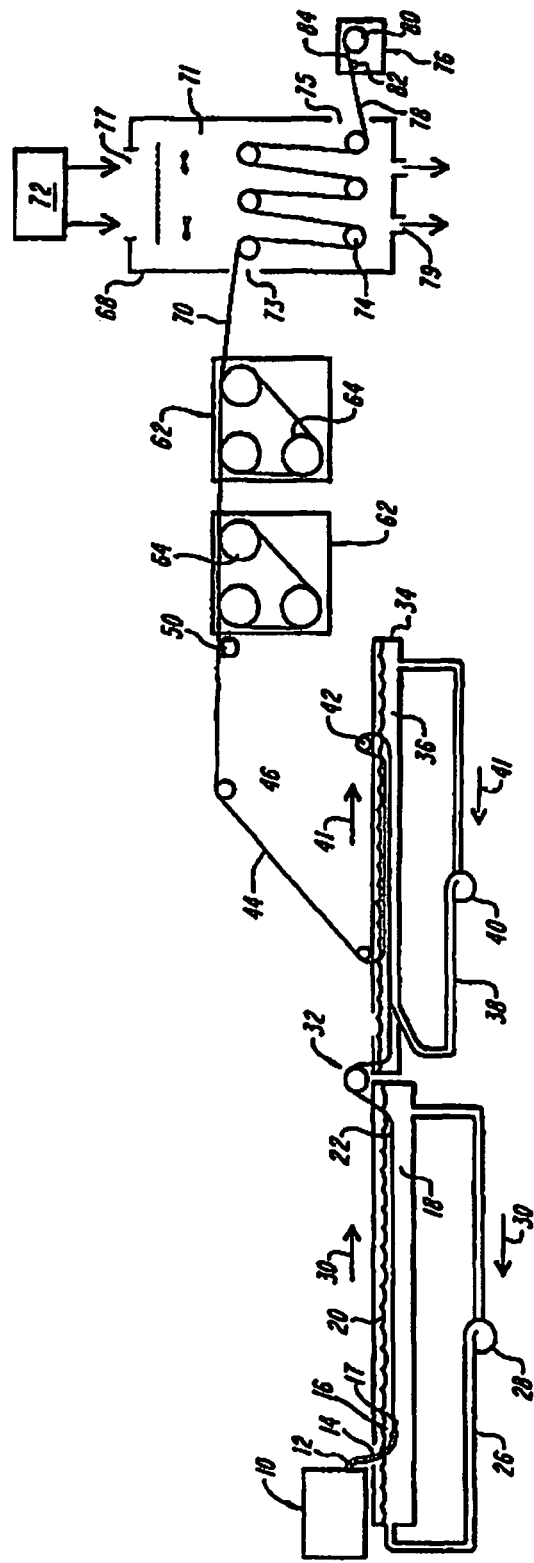
FIG. 4 is a schematic illustration of another apparatus suitable for spinning fiber in accordance with the present disclosure.

In an illustrative apparatus for gel spinning such fibers shown in FIG. 4, collagen reservoir chamber 10 holds a liquid collagen solution. In one embodiment, a suitable chamber is a stainless steel syringe. Reservoir tube 12 is attached to collagen reservoir chamber 10 for directing collagen solution from collagen reservoir chamber 10 through infusion pump 14 to spinneret 16. Infusion pump 14 is capable of raising the pressure of the collagen material such that it can be extruded through spinneret nozzle 17 of spinneret 16. In embodiments, a positive displacement metering pump is used. Spinneret 16 can be single bore or multiple bore to produce monofilament or multifilament fibers respectively. The spinneret bores can be of various diameters or have tapered profiles to form fibers of different sizes and tensile strengths. Co-component fibers can be produced with other specialized spinnerets as are known in the art. In one embodiment, spinneret nozzle 17 has diameters in the range of between about 100 and 1,000 microns.

Coagulation bath 18 has a coagulation solution 20 that can cause the liquid collagen to form a collagen gel, such as a 0.75% alkaline alginic acid in a boric acid buffer or sugar solutions or poly(ethylene glycol) solution which also has hydrophilic properties. The opening of spinneret is immersed in a flowing coagulation solution 20. Coagulation bath 18 is suitably sized for allowing extrusion of fiber from spinneret 16 through coagulation solution 20 while having a sufficient residency time for collagen gel fiber 22 to form. Coagulation bath 18 can be heated and instrumented for monitoring the relevant process variables, such as temperature, pH and velocity. Coagulation bath 18 allows collagen gel fiber 22 to be formed in a horizontal trough or in a tube or vertically in a tube. Coagulation bath 18 is configured to allow circulation of coagulation solution 20 through recirculating loop 26 by circulating pump 28. Coagulation bath flow can be in the same direction 30 of fiber travel. At the end of the coagulation bath 18, roller 32 is for directing fiber out of the coagulation bath. Roller 32 is motorized and can be activated to wind collagen gel fiber 22 and subsequently tow collagen gel fiber 22 at desired speeds.

Dehydrating bath 34 is adjacent to roller 32 and coagulation bath 18 and is configured to allow fiber 22 to be drawn into dehydrating bath 34 from roller 32. Dehydrating bath 34 holds dehydrating solution 36, such as 90% ethanol, which allows further dehydration and annealing of the fiber and promotes polymerization of the collagen to improve fiber strength. An example of another suitable dehydration solution composition is acetone. Dehydrating bath 34 is configured to allow variable circulation of dehydrating solution 36 through recirculating loop 38 by circulating pump 40 which can be adjusted directionally, such as direction 41 or in the opposite direction. Return rollers 42, which can be near each end of dehydrating bath 34, allow the fiber path to be lengthened by doubling back to make any number of multiple passes through dehydrating bath 34 to allow further dehydration and promote polymerization and/or cross-linking of the first and second precursors.

Partially dehydrated fiber 44 is wound around roller 46 to second roller 50 and then to stretching roller means 62, wherein the fiber can undergo a controlled deformation by being stretched between two groups of rollers 64 rotating at slightly different rates of speed. The speed of rotation of rollers 64 can be precisely controlled with digital microprocessors arranged in a closed feedback loop. The fibers are wrapped around each roller 64 several times to prevent fiber slippage relative to the roller surfaces. Roller 64 surfaces can be made of a polymer or a hardened metal resistant to corrosion. Roller 64 rotations can be adjusted individually to allow the fiber to be stretched beyond the elastic yield point to produce a longer fiber of reduced diameter. Stretching roller means 62 can operate under semi-dry or dry conditions and also under high moisture content atmosphere.

Drying cabinet 68 has opening 73 for receiving stretched fiber 70 from stretching rollers 62. Drying cabinet 68 has passage 71 through drying cabinet 68 for receiving warm, dry filtered air or a dry inert gas, such as dry nitrogen gas, from gas source 72 at a suitable temperature and humidity for drying stretched fiber 70. The air can be passed through air passage opening 77 into passage 71 and exiting from air passage opening 79. In embodiments, the temperature of the air is between about 35° C. and 39° C. The humidity is in the range of between 10 and 20 percent relative humidity. Drying cabinet 68 has a series of rollers 74 which allows stretched fiber 70 to remain in drying cabinet 68 while being rolled, thereby increasing the residence time of fiber 70 in drying cabinet 68. Drying cabinet rollers 74 are adjustable in distance between each other and to compensate for the fiber line speed. Drying cabinet rollers 74 can be driven at a surface roller speed that can be synchronized with that of stretching roller means 62. Drying cabinet 68 has a door to provide access to the rollers for threading the leader thread.

Take-up winder 76 is for receiving dried fiber 78 from exit 75 of drying cabinet 68. Take-up winder 76 has spool 80 for receiving dried fiber on a removable spindle bobbin. Take-up winder 76 has a slip clutch 82 to provide a constant fiber line tension and fiber line speed as the spooled fiber rotates radially around spool 80. Fiber spool 80 can wind the fiber level or by randomly winding with the take-up winder 76.

As noted previously, the first and second precursors may be contacted with UV light at one or more points in the extrusion process. For example, the solution may be irradiated with UV light as it exits spinneret nozzle 17. As another example, the fiber may be irradiated with UV light as it exits coagulation bath 20. As yet another example, the fiber may be irradiated with UV light as it is wound onto take-up winder 76. Those skilled in the art reading this diosclosure will readily envision other points during the extrusion process when UV irradiation may be applied.

Use of the Present Cross-Linked Fibers

In the present application, the terms "filaments" and "fibers" are used interchangeably. Fibers formed in accordance with the present invention may be used for a variety of surgical and wound applications. The fibers, for example, may be used alone, such as for example, for closing wounds and incisions in the form of monofilament or multifilament sutures. Multifilament sutures may be constructed using any technique within the purview of those skilled in the art, such as spinning and braiding the fibers together. The fibers may also be used in combination with the other absorbable or non-absorbable fibers to form multifilament sutures or to form knitted, woven, or non-woven meshes or fabrics. A wide variety of surgical articles can be manufactured from the fibers of the present disclosure. These include but are not limited to sutures as discussed above, threads, rods, filaments, yarns, meshes, slings, patches, wound dressings, drug delivery devices, fasteners, and other implants and composite materials, such as pledgets, buttresses, adhesion barriers, and the like.

The fibers may further be use for delivery of a bioactive agent. Thus, in some embodiments, at least one bioactive agent may be combined with either the first precursor or the second precursor and/or may be separately applied to finished fiber. The agents may be freely admixed with the precursors (making sure not reactive with them) or may be tethered to the precursors through any variety of chemical bonds. In these embodiments, the present fibers can also serve as a vehicle for delivery of the bioactive agent. The term "bioactive agent", as used herein, is used in its broadest sense and includes any substance or mixture of substances that have clinical use. Consequently, bioactive agents may or may not have pharmacological activity per se, e.g., a dye, or fragrance. Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the present fiber in any suitable form of matter, e.g., films, powders, liquids, gels and the like.

Examples of classes of bioactive agents which may be utilized in accordance with the present disclosure include anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesive agents can be used to prevent adhesions from forming between the implantable medical device and the surrounding tissues opposite the target tissue. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents which may be included as a bioactive agent of the present disclosure include triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent in the bioactive coating of the present disclosure.

Other bioactive agents which may be included as a bioactive agent in accordance with the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g. oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents which may be included in accordance with the present disclosure include viruses and cells, peptides, polypeptides and proteins, analogs, muteins, and active fragments thereof, such as immunoglobulins, antibodies, cytokines (e.g. lymphokines, monokines, chemokines), blood clotting factors, hemopoietic factors, interleukins (IL-2, IL-3, IL-4, IL-6), interferons (β-IFN, (α-IFN and γ-IFN), erythropoietin, nucleases, tumor necrosis factor, colony stimulating factors (e.g., GCSF, GM-CSF, MCSF), insulin, anti-tumor agents and tumor suppressors, blood proteins, fibrin, thrombin, fibrinogen, synthetic thrombin, synthetic fibrin, synthetic fibrinogen, gonadotropins (e.g., FSH, LH, CG, etc.), hormones and hormone analogs (e.g., growth hormone), vaccines (e.g., tumoral, bacterial and viral antigens); somatostatin; antigens; blood coagulation factors; growth factors (e.g., nerve growth factor, insulin-like growth factor); bone morphogenic proteins, TGF-B, protein inhibitors, protein antagonists, and protein agonists; nucleic acids, such as antisense molecules, DNA, RNA, RNAi; oligonucleotides; polynucleotides; and ribozymes.

Devices formed with the fibers of the present disclosure, such as a mesh, may be at least partially coated with a bioresorbable coating by a surface treatment for enhanced properties. For example, the coating may be collagen, chitosan, polysaccharides, or mixtures thereof. The polysaccharides may be hyaluronic acid, alginic acid, polyglucuronic acid, chitosan, starch, soluble cellulose derivatives, and mixtures thereof. Such a coating makes it possible to eliminate crevices which may form during the construction and interplay of the fibers where bacteria or inflammatory cells may develop, thus making it possible to reduce the risk of inflammation and sepsis by preventing the installation of undesirable bacteria and/or microorganisms and/or inflammatory cells into the filled or covered crevices.

While several embodiments of the disclosure have been described, it is not intended that the disclosure be limited thereto, as it is intended that the disclosure be as broad in scope as the art will allow and that the specification be read likewise. Therefore, the above description should not be construed as limiting, but merely as exemplifications of embodiments. Those skilled in the art will envision other modifications within the scope and spirit of the claims appended hereto.

What is claimed is:

1. A process of forming a cross-linked filament for a surgical device comprising:
    mixing first and second precursors, each of the first and second precursors possessing a polyol core and functionalized with at least one functional group having click reactivity when exposed to UV radiation, wherein the at least one functional group of the first precursor is a thiol group and the at least one functional group of the second precursor is an alkene group; and
    extruding the first and second precursors through an extrusion unit to produce a filament,
    exposing the first and second precursors to UV radiation during the extruding process.

2. The process of claim 1, wherein the polyol core of the first precursor is selected from the group consisting of polyethers, polyesters, polyether-esters, polyalkanols, and combinations thereof.

3. The process of claim 1, wherein the polyol core of the second precursor is selected from the group consisting of polyethers, polyesters, polyether-esters, polyalkanols, and combinations thereof.

4. The process according to claim 1, wherein exposing the first and second precursors to UV radiation occurs while in a molten state.

5. The process according to claim 1, wherein exposing the first and second precursors to UV radiation occurs after forming the filament.

6. The process according to claim 1, wherein exposing the first and second precursors to UV radiation further comprises passing the filament through a quench bath irradiated with a UV light.

7. The process according to claim 1, wherein the polyol core of the first precursor comprises a poly(ethylene glycol) with a molecular weight from about 200 g/mol to about 10000 g/mol.

8. The process according to claim 1, wherein the polyol core of the first precursor comprises a poly(ethylene glycol) with a molecular weight from about 400 g/mol to about 900 g/mol.

9. The process according to claim 1, wherein the polyol core of the second precursor comprises a poly(ethylene glycol) with a molecular weight from about 200 g/mol to about 10000 g/mol.

10. The process according to claim 1, wherein the polyol core of the second precursor comprises a poly(ethylene glycol) with a molecular weight from about 400 g/mol to about 900 g/mol.

11. The process according to claim 1, wherein the polyol core of the first precursor and the polyol core of the second precursor are different.

12. The process according to claim 1, wherein the at least one functional group of the first precursor and the at least one functional group of the second precursor are present in a ratio of about 1:2 to 1:1.

* * * * *